United States Patent [19]

Mayerhoefer et al.

[11] 4,143,101

[45] Mar. 6, 1979

[54] 5,5-BIS(HALOMETHYL)1,3,2-DIOXAPHOS-PHORINANE COMPOUNDS

[75] Inventors: Horst Mayerhoefer, Oberwil; Rainer Wolf, Allschwil, both of Switzerland

[73] Assignee: Sandoz Ltd., Basel, Switzerland

[21] Appl. No.: 180,498

[22] Filed: Sep. 14, 1971

[30] Foreign Application Priority Data

Sep. 25, 1970 [CH] Switzerland .................. 14264/70
Jan. 26, 1971 [CH] Switzerland .................... 1119/71
Jul. 23, 1971 [CH] Switzerland .................. 10879/71

[51] Int. Cl.$^2$ ............................................. C07F 9/15
[52] U.S. Cl. ........................... 260/927 R; 260/45.8 R; 260/937
[58] Field of Search ..................... 260/927 R, 937

[56] References Cited

U.S. PATENT DOCUMENTS

| | | | |
|---|---|---|---|
| 3,033,888 | 5/1962 | Wadsworth et al. | 260/937 |
| 3,159,664 | 12/1964 | Bartlett | 260/937 |
| 3,467,733 | 9/1969 | Dever et al. | 260/927 R |
| 3,597,503 | 8/1971 | Wilson et al. | 260/937 |
| 3,887,655 | 6/1975 | Shim | 260/937 |

*Primary Examiner*—Richard Raymond
*Attorney, Agent, or Firm*—Gerald D. Sharkin; Richard E. Vila; Thomas C. Doyle

[57] ABSTRACT

This invention relates to the production of phosphorus derivatives with a 5,5-bis-(halomethyl)-1,3,2-dioxaphosphorinane structure and to their use as flameproofing agents for plastics and textile fibres.

26 Claims, No Drawings

5,5-BIS(HALOMETHYL)1,3,2-DIOXAPHOSPHORINANE COMPOUNDS

This invention relates to the production of phosphorus derivatives with a 5,5-bis-(halomethyl)-1,3,2-dioxaphosphorinane structure and to their use as flameproofing agents for plastics and textile fibres.

These phosphorus derivatives are of the general formula $$\left[ \begin{array}{c} Hal-CH_2 \\ Hal-CH_2 \end{array} \diagdown C \diagup \begin{array}{c} CH_2-O \\ CH_2-O \end{array} \diagdown P-Z \right]_n R_1 \quad \text{(I),}$$

where
Hal stands for chlorine or bromine,
Y for O or S,
Z for O, S or $$-\underset{|}{N}-R_2,$$

$R_1$ for an n-valent aliphatic, cycloaliphatic, aromatic or heterocyclic radical which may be substituted,
$R_2$ for H or a monovalent aliphatic, cycloaliphatic, aromatic or heterocyclic radical which may be substituted,
n for a whole number and
m for 1 or 2.

The compounds conforming to this invention can be produced by the reaction of
(a) 1 mol of a compound of formula $$\left( \begin{array}{c} Hal \\ Hal \end{array} \diagdown P-Z \right)_n R_1 \quad \text{(II),}$$

with n mols of a compound of formula $$\begin{array}{c} Hal-CH_2 \\ Hal-CH_2 \end{array} \diagdown C \diagup \begin{array}{c} CH_2-OH \\ CH_2-OH \end{array} \quad \text{(III),}$$

or
(b) 1 mol of a compound of formula $$R_1-(ZH)_n \quad \text{(IV)}$$

with n mols of a compound of formula $$\begin{array}{c} Hal-CH_2 \\ Hal-CH_2 \end{array} \diagdown C \diagup \begin{array}{c} CH_2-O \\ CH_2-O \end{array} \diagdown P-Hal \quad \text{(V)}$$

where $R_1$, Hal, Z, Y, m and n have the aforestated meanings.

The starting compounds of general formula (V) can be produced as described, for example, in Example A below.

EXAMPLE A

A mixture of 392 parts of pentaerythrite dibromohydrin and 237 parts of pyridine in 428 parts of diethylether is dropped with vigorous stirring into a solution of 205.5 parts of distilled phosphorus trichloride in 428 parts of diethyl ether in 2 hours at −5° C. The reaction is carried out under nitrogen. As it proceeds a white precipitate settles out. The total reaction time is 4 hours at −5° C. After separation from the precipitate, the filtrate is concentrated by evaporation and distilled at high vacuum, on which a colourless oil is isolated.

B.P.$_{0.45}$ 129°–131° C.

$C_5H_8Br_2ClO_2P$ (326.36) Calc. C 18.4, H 2.5, Br 49.0, Cl 10.9, P 9.5. Found C 18.8, H 2.7, Br 48.8, Cl 11.1, P 9.8.

Preferred among the compounds of the general formula (II) are the compounds having the formulae $$Q-Z-\underset{\underset{O(S)}{\|}}{P}Cl_2 \quad \text{(VI)}$$

and $$Cl_2\underset{\underset{O(S)}{\|}}{P}-O-M-O-\underset{\underset{O(S)}{\|}}{P}Cl_2 \quad \text{(VII).}$$

In formula (VI) the radical Q represents a hydrocarbon or halogenated hydrocarbon radical such as methyl, ethyl, n-propyl, iso-propyl, n-butyl, iso-butyl, tert.butyl, hexyl, β-chloroethyl, β-bromethyl, 2,3-dichloropropyl, 2,3-dichloropropyl, 2,3-dibromopropyl, cyclohexyl, phenyl, diphenyl, α-naphthyl, β-naphthyl, 2-chlorophenyl, 3-chlorophenyl, 4-chlorophenyl, 2,4-dichlorophenyl, 2,4,5-trichlorophenyl, 2,4,6-trichlorophenyl, 2,3,4,5-tetrachlorophenyl, pentachlorophenyl, 2-bromophenyl, 3-bromophenyl, 4-bromophenyl, 2,4-dibromophenyl, 2,4,6-tribromophenyl or pentabromophenyl, while the radical Z in this formula has one of the aforestated meanings.

In formula (VII) the bridge member M may represent, for example,

-{cyclohexyl-H}-, -{phenyl}-,

-{phenyl}-(L)$_{x-1}$-{phenyl}- where L may be, for instance, -CH$_2$CH$_2$-, $$-\underset{\underset{CH_3}{|}}{\overset{\overset{CH_3}{|}}{C}}-,$$

O, S or SO$_2$ and x is 1 or 2, or M may represent a substituted bridge member such as

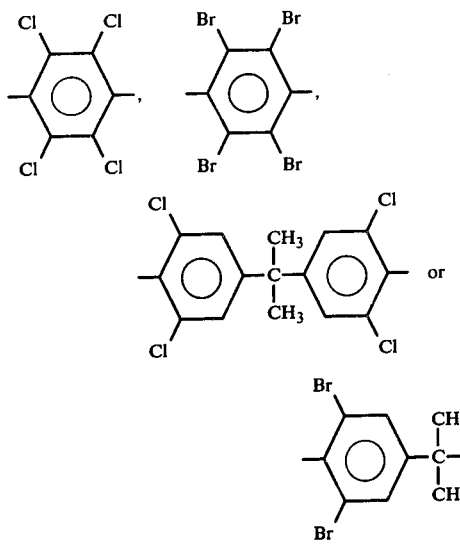

The compound of general formula (III) is either 2,2-bis-(chloromethyl)-1,3-propanediol or 2,2-bis-(bromomethyl)-1,3-propanediol.

A large number of alcohols, phenols, mercaptans, thiophenols, primary or secondary amines, anilines, glycols, polyols, polythiols or polyamines can be employed as compounds of general formula (IV).

Examples of compounds of general formula (V) are 2-chloro-2-oxo-5,5-bis-(chloromethyl)-1,3,2-dioxaphosphorinane, 2-chloro-2-thiono-5,5-bis-(chloromethyl)-1,3,2-dioxaphosphorinane, 2-chloro-2-thiono-5,5-bis-(bromomethyl)-1,3,2-dioxaphosphorinane and 2-chloro-5,5-bis-(bromomethyl)-1,3,2-dioxaphosphorinane.

The reactions are best carried out in an organic solvent which is inert to the phosphorus halides and in the presence of an acid binding agent. The reaction temperature can range from −50° C. to 200° C., or preferably 0° C. to 100° C., optionally under increased or reduced pressure.

The reaction can be allowed to proceed at a relatively low temperature and heating applied at the end in order to stop the reaction.

The organic solvents suitable for use in the process include ethers such as dioxane, 1,2-dimethoxy- and 1,2-diethoxy-ethane, 1-ethoxy-2-(2′-ethoxy)-ethane, tetrahydrofuran; aromatic hydrocarbons such as benzene, toluene, xylene, mesitylene; halogenated aliphatic and aromatic hydrocarbons such as chloroform, trichloroethylene, chlorobenzene, ortho-dichlorobenzene, bromobenzene; ketones such as propanone-2, butanone-2, 4-methylpentanone-2, 2,6dimethyl heptanone-4; also acetonitrile, dimethyl formamide, dimethyl acetamine, dimethyl sulphoxide, tetramethylene sulphone, phosphoric acid tris-(dimethylamide),.

The following are examples of suitable acid-binding agents: the hydroxides and carbonates of alkali metals such as potassium, sodium and lithiumhydroxide rsp. carbonate, and hydroxides and carbonates of alkaline-earth metals such as calcium, magnesium and barium hydroxide resp. carbonate, ammonium hydroxide, ammonium carbonate, quaternary ammonium hydroxides such as benzyltrimethyl, tribenzylmethyl and tetra-(lower alkyl)ammonium hydroxide, guanidines and diguanidines such as hexa- and hepta-(lower alkyl)-diguanidine, tetra-(lower alkyl)-guanidine, tri-(lower alkyl)-amines such as triethylamine, tributylamine and trimethylamine, pyridine,.

If tertiary amines are chosen as acid-binding agents they can also serve as solvents.

On completion of the reaction the product can be precipitated by diluting the medium with a suitable agent, preferably water optionally adding an acid, or by the addition of an alcohol such as methanol, ethanol or iso-propanol, after which the precipitate is filtered with suction and dried. Alternatively the solvent can be removed by distillation, preferably under reduced pressure, and the residue washed with water or recrystalized from a suitable agent.

The products synthesised by the process of this invention are normally obtained in the form of colourless, crystalline water-insoluble solids, which generally are readily soluble in organic solvents. A number of these compounds are specified in Table I.

Table I

| Structure | M.P. ° C. | Analysis |
|---|---|---|
| (VIII) | 138 | Calc. Br:39.9 P:7.8<br>Found Br:39.7 P:8.1 |
| (IX) | 137 | Calc. Br:36.7 Cl:8.1 P:7.1<br>Found Br:36.3 Cl:7.9 P:7.3 |
| (X) | 129 | Calc. Br:34.0 Cl:15.3 P:6.6<br>Found Br:33.4 CL:15.4 P:6.6 |

Table I-continued

| Structure | M.P. °C. | Analysis |
|---|---|---|
| (XI) 2,4,5-trichlorophenyl bis(3-bromo-2,2-bis(bromomethyl)propyl) phosphate | 163 | Calc. Br:31.7 Cl:21.2<br>Found Br:31.8 Cl:20.6 |
| (XII) pentachlorophenyl bis(3-bromo-2,2-bis(bromomethyl)propyl) phosphate | 225 | Calc. Cl:31.0 P:5.4<br>Found Cl:31.7 P:5.6 |
| (XIII) pentachlorophenyl bis(3-chloro-2,2-bis(chloromethyl)propyl) phosphate | 217 | Calc. Cl:51.3 P:6.4<br>Found Cl:49.8 P:6.2 |
| (XIV) 4-bromophenyl bis(3-bromo-2,2-bis(bromomethyl)propyl) phosphate | 135 | Calc. Br:50.5 P:6.5<br>Found Br:50.0 P:6.5 |
| (XV) 2,4,6-tribromophenyl bis(3-bromo-2,2-bis(bromomethyl)propyl) phosphate | 195 | Calc. Br:62.9 P:4.8<br>Found Br:62.6 P:4.9 |
| (XVI) pentabromophenyl bis(3-bromo-2,2-bis(bromomethyl)propyl) phosphate | 261 | Calc. Br: 69.9 P:3.9<br>Found Br:69.5 P:3.8 |
| (XVII) tetrabromohydroquinone bis-phosphate derivative | 215 | Calc. Br:61.7 P:6.0<br>Found Br:60.7 P:7.1 |
| (XVIII) bisphenol-A bis-phosphate derivative | 161 | Calc. Br:38.1 P:7.4<br>Found Br:38.4 P:7.8 |
| (XIX) tetrabromobisphenol-A bis-phosphate derivative | 215 | Calc. Br:55.3 P:5.3<br>Found Br:55.1 P:4.6 |

Table I-continued

| Structure | M.P. °C. | Analysis |
|---|---|---|
| CH₃(CH₂)₇—O—P(=O)(OCH₂)₂C(CH₂Br)₂  (XX) | 70 | Calc. Br:43.7 P:8.5<br>Found Br:42.1 P:8.6 |
| C₆H₅—O—P(=O)(OCH₂)₂C(CH₂Cl)₂  (XXI) | 140 | Calc. Cl:22.8 P:9.9<br>Found Cl:22.7 P:9.9 |
| 4-Cl-C₆H₄—O—P(=O)(OCH₂)₂C(CH₂Cl)₂  (XXII) | 132 | Calc. Cl:30.9 P:8.7<br>Found Cl:30.5 P:9.0 |
| 4-Br-C₆H₄—O—P(=O)(OCH₂)₂C(CH₂Cl)₂  (XXIII) | 118 | Calc. Br:20.5 Cl:18.2 P:7.9<br>Found Br:20.5 Cl:18.2 P:7.8 |
| 2,4,6-Br₃-C₆H₂—O—P(=O)(OCH₂)₂C(CH₂Cl)₂  (XXIV) | 205 | Calc. Br:43.7 Cl:12.9 P:5.6<br>Found Br:43.0 Cl:12.2 P:5.9 |
| 2-naphthyl—O—P(=O)(OCH₂)₂C(CH₂Br)₂  (XXV) | 170 | Calc. Br:35.6 P:6.9<br>Found Br:35.6 P:7.1 |
| 1-naphthyl—O—P(=O)(OCH₂)₂C(CH₂Br)₂  (XXVI) | 153 | Calc. Br:35.6 P:6.9<br>Found Br:35.8 P:6.9 |
| (ClCH₂)₂CH—O—P(=O)(OCH₂)₂C(CH₂Br)₂  (XXVII) | 55 | Calc. Br:36.8 Cl:16.3 P:7.1<br>Found Br:36.0 Cl:16.6 P:7.8 |
| ClCH₂CH₂—O—P(=O)(OCH₂)₂C(CH₂Br)₂  (XXVIII) | 63 | Calc. Br:41.2 Cl:9.1 P:8.0<br>Found Br:40.8 Cl:9.3 P:8.0 |
| (BrCH₂)₃C—CH₂—O—P(=O)(OCH₂)₂C(CH₂Br)₂  (XXIX) | 160 | Calc. Br:63.2 P:4.9<br>Found Br:63.5 P:4.9 |

Table I-continued

| Structure | M.P. °C. | Analysis |
|---|---|---|
| (XXX) 2,4,6-tribromophenyl-NH-P(=O)(OCH₂)₂C(CH₂Br)₂ | 205 | Calc. Br:62.7 N:2.2 P:4.9<br>Found Br:62.5 N:2.3 P:4.9 |
| (XXXI) (BrCH₂)₂C(CH₂O)₂P-OC₂H₅ | | Calc. Br:47.6 P:9.2<br>Found Br:47.6 P:8.9 |
| (XXXII) 4-bromophenyl-NH-P(=O)(OCH₂)₂C(CH₂Br)₂ | 224 | Calc. Br:50.2 N:2.9 P:6.5<br>Found Br:49.4 N:3.0 P:6.6 |
| (XXXIII) 4-bromophenyl-NH-P(=O)(OCH₂)₂C(CH₂Cl)₂ | 224 | Calc. Br:20.6 Cl:18.2 N:3.6 P:8.0<br>Found Br:20.6 Cl:17.8 N:3.6 P:8.5 |
| (XXXIV) 2,4-dibromophenyl-NH-P(=O)(OCH₂)₂C(CH₂Br)₂ | 150 | Calc. Br:57.3 N:2.5 P:5.6<br>Found Br:57.7 N:2.6 P:5.8 |
| (XXXV) 2,4-dibromophenyl-NH-P(=O)(OCH₂)₂C(CH₂Cl)₂ | 143 | Calc. Br:34.2 Cl:15.2 H:3.0 P:6.6<br>Found Br:34.0 Cl:14.8 H:3.1 P:6.5 |
| (XXXVI) 2,4,6-tribromophenyl-NH-P(=O)(OCH₂)₂C(CH₂Cl)₂ | 182 | Calc. Br:43.8 Cl:13.0 N:2.6 P:5.7<br>Found Br:43.9 Cl:12.9 N:2.9 P:5.6 |
| (XXXVII) 4-chlorophenyl-NH-P(=O)(OCH₂)₂C(CH₂Br)₂ | 222 | Calc. Br:36.9 Cl:8.2 N:3.2 P:7.2<br>Found Br:36.9 Cl:8.1 N:3.2 P:7.2 |
| (XXXVIII) 2,4,6-trichlorophenyl-NH-P(=O)(OCH₂)₂C(CH₂Br)₂ | 202 | Calc. Br:31.8 Cl:21.2 N:2.8 P:6.2<br>Found Br:31.7 Cl:20.8 N:2.8 P:5.9 |
| (XXXIX) 4-chlorophenyl-NH-P(=O)(OCH₂)₂C(CH₂Cl)₂ | 219 | Calc. Cl:30.9 N:4.1 P:9.0<br>Found Cl:31.0 N:4.2 P:8.7 |

Table I-continued
| Structure | M.P. °C. | Analysis |
|---|---|---|
| (XL) | 58 | Calc. Br:27.7 P:5.3<br>Found Br:26.5 P:5.4 |
| (XLI) | 135.5 | Calc. Br:46.4 P:9.0<br>Found Br:45.6 P:9.2 |
| (XLII) | 225 | Calc. Br:63.6 P:6.2<br>Found Br:63.0 P:6.5 |
| (XLIII) | 187 | Calc. Br:56.9 P:5.5<br>Found Br:56.4 P:5.7 |
| (XLIV) | 184 | Calc. Br:33.8 P:6.6<br>Found Br:33.6 P:6.7 |
| (XLV) | 74–75 | Calc. Br:42.5 P:8.2<br>Found Br:42.3 P:8.0 |
| (XLVI) | 92 | Calc. Br:65.0 P:5.1<br>Found Br:64.7 P:5.3 |
| (XLVII) | 108 | Calc. Br:64.4 P:5.0<br>Found Br:63.2 P:5.3 |
| (XLVIII) | 95–97 | Calc. Br:57.0 P:7.4<br>Found Br:55.6 P:7.3 |
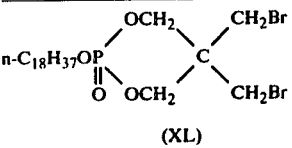
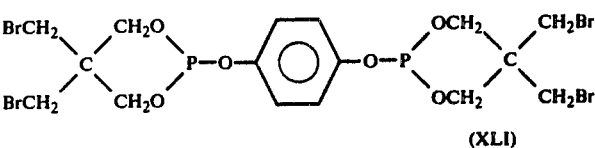
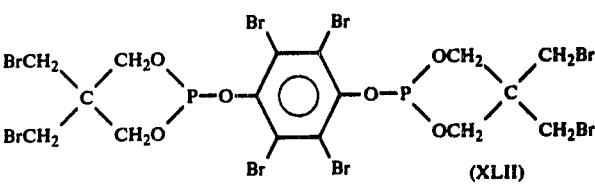
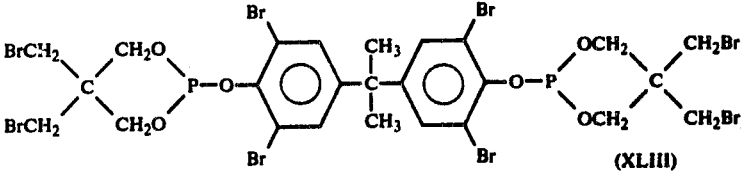
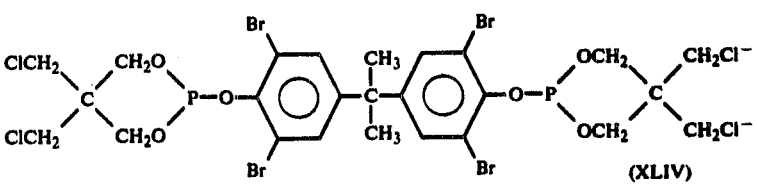
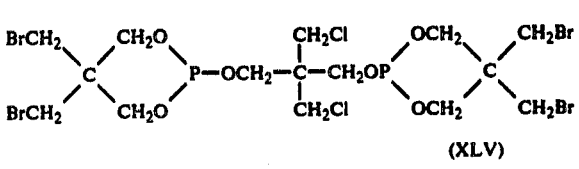
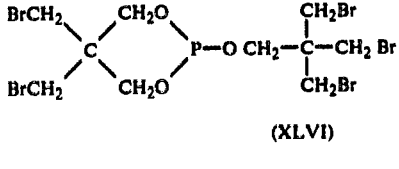
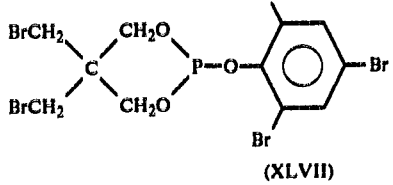
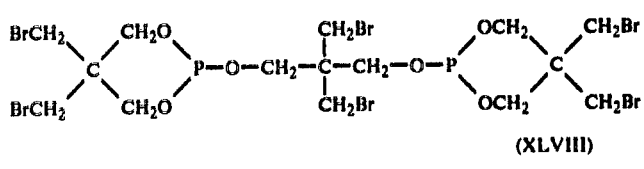

Table I-continued

| Structure | M.P. °C. | Analysis |
|---|---|---|
| 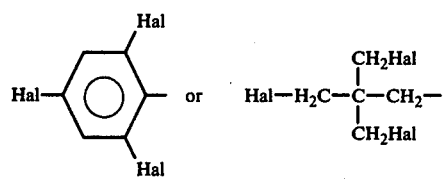 (XLIX) | 240 | Calc. Br:38.6 P:7.5<br>Found Br:38.5 P:7.3 |

The disclosed compounds are highly effective as flameproofing additives in synthetic fibres and plastics such as polyethylene, polypropylene, polyvinyl chloride and polystyrene.

The preferred compounds of formula (I) are those in which n is 1 or 2 and when n is 2, Z is 0. If m represents 2, Z may be either 0 or NH and $R_1$ may be an n-valent aliphatic, optionally halosubstituted radical or an optionally halo-, alkyl- or haloalkyl-substituted aromatic radical. If m represents 1, Z is 0 and $R_1$, when n is 1, represents

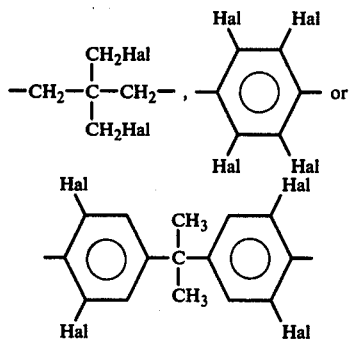

or, when n is 2, $R_1$ represents

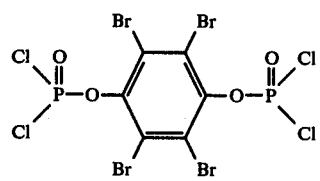

Compounds X, XI, XIV, XV, XVI, XVII, XIX, XXIX, XXXII, XXXIII, XXXV, XXXVI, XXXIX, XL, XLII, XLIII, XLIV, XLV, XLVI and XLIX of Table I are, among all compounds of formula (I), particularly effective as flameproofing additives.

The claimed compounds are especially suitable as additives to spinning solutions and melts and to injection moulding materials, provided they are not volatile at the spinning or moulding temperatures.

In the following Examples, which illustrate the invention without limiting its scope, the parts and percentages are by weight and the temperatures in degrees centigrade.

EXAMPLE 1

At room temperature 42 parts of pyridine are dropped into a solution of 60 parts of phosphoric acid-(4-chlorophenylester)-dichloride and 63 parts of 2,2-bis-(bromomethyl)-1,3-propanediol in 220 parts of tetrahydrofuran. The reaction mixture is then stirred for 2 hours at room temperature and subsequently for 20 hours at 50°. During the reaction pyridine hydrochloride settles out. On completion of the reaction the tetrahydrofuran is removed with vacuum, the residue is mixed with water, and the product isolated by filtration and washed with water. Approximately 100 parts of compound (IX) (Table I) are obtained, which is equal to about 94% of the theoretical yield.

EXAMPLE 2

128 Parts of the compound of formula

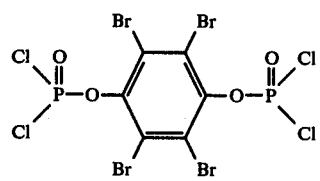

are dissolved and 104 parts of 2,2-bis-(bromomethyl)-1,3-propanediol suspended in 220 parts of tetrahydrofuran. At room temperature 63.5 parts of pyridine are added dropwise. The reaction mixture is then stirred at room temperature for 5 hours and during the next 20 hours at 50°. In the course of the reaction pyridine hydrochloride, together with the reaction product, settles out. The tetrahydrofuran is distilled in a Rotavapor apparatus, the residue mixed with water, and the product filtered and washed with water and ethanol. The compound of formula (XVII) (Table I) is obtained in a yield of about 177 parts, which is about 94% of theory.

Synthesis of the compounds VIII, X to XVI and XVIII to XXIX is carried out in analogy with Examples 1 and 2.

EXAMPLE 3

A solution of 29.3 parts of pentaerythrite dibromohydrin, 17.7 parts of pyridine (abs.) and 88 parts of tetrahydrofuran (abs.) is dropped in 20 minutes with stirring into a solution of 50 parts of phosphoric acid tribromanilide dichloride in 221 parts of tetrahydrofuran (abs.) under a nitrogen atmosphere. In the resulting slightly exothermic reaction a white precipitate is formed. The total reaction time is 18 hours. Subsequently the solid substance is filtered off and the filtrate freed from tetrahydrofuran. The remaining solid product (compound XXX of Table I) is recrystallized from methanol and has a melting point of 205°.

EXAMPLE 4

48.8 Parts of 2-chloro-5,5-bis-(bromomethyl)-1,3,2-dioxaphosphorinane are dissolved in 143 parts of diethylether (abs.) under nitrogen. In one hour at 10° a solution of 6.9 parts of ethanol (abs.), 11.9 parts of pyridine (abs.) and 36 parts of diethylether (abs.) is added dropwise causing a white precipitate to settle out. On completion of the addition stirring is continued for further 3 hours at room temperature. At this point 107 parts of diethylether are added, the solid substance removed by filtration and the filtrate freed from diethylether. The colourless oil which remains (49.1 parts of compound XXXI of Table I) is either submitted to column chromatography (aluminum oxide, neutral, Active Stage I, manufacturer Woelm) or to high vacuum distillation in a molecular distillation apparatus. B.p.$_{0.001}$ = 50° C.

EXAMPLE 5

A solution of 56.3 parts of pentaerythrite dibromohydrin, 34 parts of pyridine and 178 parts of tetrahydrofuran (abs.) is dropped into a solution of 62.1 parts of phosphoric acid-4-bromanilide in 356 parts of tetrahydrofuran (abs.) in 20 minutes at 20° with stirring under a nitrogen atmosphere. The mixture is allowed to react for 16 hours at 30°. The white precipitate formed is filtered off and the filtrate freed from tetrahydrofuran. The pale orange coloured product left (compound XXXII of Table I) is washed with 740 parts of chloroform and then with 79 parts of methanol.

EXAMPLE 6

A solution of 60.2 parts of pentaerythrite dibromohydrin, 36.3 parts of pyridine (abs.) and 133 parts of tetrahydrofuran (abs.) is dropped in 20 minutes at 20° with stirring into a solution of 56.2 parts of phosphoric acid-4-chloranilide dichloride in 257 parts of tetrahydrofuran (abs.) under nitrogen. The mixture is allowed to react for 16 hours at 30°. After separation of a white precipitate, the filtrate is concentrated by evaporation in a Rotavapor apparatus, on which a clear oil is obtained. The oil is treated with 740 parts of chloroform, which yields a white solid (compound XXXVII of Table I).

EXAMPLE 7

A solution of 109 parts of tetrabromo-bis-phenol-A in 641 parts of tetrahydrofuran is added to 130.5 parts of 2-chloro-5,5-bis-(bromomethyl)-1,3,2-dioxaphosphorinane under nitrogen. After cooling to 5° 40.4 parts of triethylamine are added dropwise within 40 minutes, keeping the inside temperature below 15°. The reaction is allowed to continue for 16 hours at room temperature with stirring. A white precipitate settles out which is filtered off, and the filtrate is freed from solvent to give 244.7 parts of a colourless oil. The oil is dissolved in 1055 parts of benzene and precipitated from 1900 parts of ethanol in the form of white crystals (compound XLIII in Table I), which are filtered with suction, washed with ether and dried.

EXAMPLE 8

A solution of 8.65 parts of pentaerythrite dichlorodhydrin, 7.9 parts of pyridine and 35.5 parts of diethylether (abs.) are dropped into a solution of 32.6 parts of 2-chloro-5,5-bis-(bromomethyl)-1,3,2-dioxaphosphorinane in 35.5 parts of diethylether (abs.) under nitrogen at room temperature with stirring. A white precipitate settles out. The mixture is allowed to react further for 5 hours at room temperature. After filtration of the white precipitate and washing it with diethylether (abs.), the volume of the solution is made up to 318 parts with diethylether (abs.). The solution is chromographed in a column filled with 210 parts of neutral aluminium oxide, Activity Stage I, manufactured by the firm Woelm. Subsequently the column is washed with 142 parts of diethyl ether. After removal of the solvent, 16.4 parts of a white crystalline solid remain (compound XLV in Table I).

EXAMPLE 9

A solution of 32.5 parts of pentaerythrite tribromohydrin (tris-2,2,2-(bromomethyl)-ethanol) in 87 parts of toluene is added to 32.6 parts of 2-chloro-5,5-bis-(bromomethyl)-1,3,2-dioxaphosphorinane under nitrogen. After cooling to 0°, a solution of 10.1 parts of triethylamine in 43 parts of toluene is added at a rate at which the inside temperature does not increase to above 10°. The reaction is then allowed to proceed for 16 hours at room temperature. The precipitate formed is filtered off. After removal of the solvent from the filtrate 62 parts of a yellowish oil are left which solidifies on standing. It is converted into white crystals (compound XLVI in Table I) by recrystallization or washing with hexene.

EXAMPLE 10

The compound XIV listed in Table I was added to batches of the low density polyethylene at a concentration of 2% with the addition of an equal percentage by weight of antimony trioxide and a concentration of 4% without the addition of antimony trioxide. This material was injection moulded as panels of 1.2 mm thickness. In the test specified in German Industrial Standard 53438 the panels show no discoloration and are self-extinguishing. In contrast to this result, panels made of the same material containing respectively 2% and 4% of tris-(dibromopropyl)-phosphate, a known flameproofing agent, shown burning throughout their length in this test.

EXAMPLE 11

The compound XVI was throughly mixed with the polypropylene powder in a shaking machine and processed on a roller mill at 155° as hides. The hides were extruded as panels of 1 mm thickness in a moulding cycle of 2 minutes 30 seconds at 90°, first at a pressure of 2 metric tons, then at 30 tons pressure. The panels containing 4% of the additive of this invention withstood German Industrial Standard test 53438 without combustion.

EXAMPLE 12

The compound XXXII was incorporated in polypropylene as described in Example 11 and the material injection moulded as panels. The panels containing 8% of the additive were non-flammable in German Industrial Standard test 53438.

The known flameproofing agent tris-(dibromopropyl)-phosphate was dissolved in either and the solution mixed with polypropylene powder. The solvent was distilled in a rotary evaporator under vacuum leaving the polypropylene-additive mixture. This was injection moulded as panels as described in Example 11. Even with 8% of this known additive the panels were flammable in the aforementioned test.

EXAMPLE 13

The compounds XXXII and XXXIII and tris-(dibromopropyl)-phosphate, a known flameproofing agent, were incorporated in low density polyethylene by treatment in a laboratory kneading machine for 10 minutes at 150°. The material was injection moulded in a 5 minute cycle at 160° at 10 metric tons pressure. The mouldings were submitted to the German Industrial Standard test 53438 for flammability. The moulding containing compound XXXIII was self-extinguishing after a burning distance of 1 cm, the one containing compound XXXII after 2.5 cm. The moulding containing tris-(dibromopropyl)-phosphate burned over a length of 7 cm before self-extinction took place.

EXAMPLE 14

140 Parts of a compound of formula (XIX) and 14 parts of a dispersing agent based on an alkali-metal salt of a dialkylphenol polyglycol ether carboxylic acid were mixed with 246 parts of water. The mixture was ground for 5 hours in a laboratory bead mill in the presence of 400 parts of quartzite beads, with ice cooling. A fine dispersion containing 35% of the compound of formula XIX was formed, which was passed through a glass frit to free it from the beads.

This dispersion was used as a component of a padding liquor of the composition:
(A)
575 g/l of the stated 35% dispersion equivalent to 200 g/l of the compound of formula XIX
100 g/l of a trimethylol melamine trimethylether condensate
10 g/l of ammonium phosphate
The liquor was padded on a 67/33% polyester/cotton blend fabric of 165 g/m² weight at an expression giving a liquor pick-up of 75–80%. After intermediate drying for 6 minutes at 100° the resin finish was cured for 5 minutes in dry heat at 160°.

A sample of the fabric was washed once for 30 minutes at 60° with a domestic detergent and dried for 6 minutes at 100°. A second sample was washed and dried ten times in succession under the same conditions. The sample were conditioned in standard atmosphere for 24 hours, after which their flammability was tested using German Industrial Standard test 53906, in which samples of 250 × 100 mm in size are mounted on glass-fibre felt and exposed for 6 second to the ignition source.

EXAMPLE 15

Compound XXXIV was dissolved in dioxan to give a 200 g/l solution which was padded on a 67/33% polyester/cotton blend fabric of 165 g/cm² weight at a liquor pick-up of about 80%. After intermediate drying for 6 minutes at 100° a liquor of 100 g/l of a trimethylol melamine methylester condensate and 10 g/l ammonium sulphate was applied to the fabric by padding. After preliminary dry heat treatment for 6 minutes at 100° the resin finish was cured for 5 minutes at 160°.

As in Example 14, one sample of the fabric was washed and dried once and a second sample ten times under the same conditions. After conditioning in standard atmosphere the samples were tested for flammability as in Example 14.

EXAMPLE 16

The compound XI was incorporated in polypropylene at 8% concentration and the polypropylene melt spun at 270°. The filament was cold drawn and converted into twist yarn which was knit into tubular fabric. The appropriate German Industrial Standard test 53906 was carried out using an uncut sample of double fabric thickness. This sample was not flammable, whereas samples of fabric produced in the same way but without a flameproofing agent were flammable and burned completely in the test.

Example X (known compound)

A 67/33% polyester/cotton blend fabric of 165 g/m² weight was padded with a liquor of the composition:
250 g/l of a commercial flameproofing agent based on tetrakis-(hydroxymethyl)phosphonium chloride (80%)
25 g/l sodium hydroxide
50 g/l urea
70 g/l of a trimethylol melamine trimethylether condensate.
The liquor pick-up was about 75–80% and the further treatment of the fabric was as described in Example 14.

Example Y (known compound)

As described in Example X, the same polyester/cotton blend fabric was padded with a finishing liquor or a composition as given in the manufacturer's recommendations, namely:
300 g/l of a commercial flameproofing agent on an N-methylated dialkyl phosphonopropionic acid amide
15 g/l urea
5 g/l ammonium chloride
100 g/l of a trimethylol melamine trimethylether condensate.
The fabric was dried for 6 minutes at 100° and the finishing cured for 5 minutes at 180° as recommended by the manufacturer. The further treatment and the test for flammability were carried out as in Example 14.

Example Z (known compound)

A polyester/cotton blend fabric as used in the preceding Examples was finished with a 200 g/l alcoholic solution of the commercial flameproofing agent tris-(dibromopropyl)-phosphate as specified in Example 15. After intermediate drying for 6 minutes at 100° the fabric was padded with a liquor of 100 g/l of a trimethylol melamine trimethylether condensate and 10 g/l ammonium sulphate as described above. The further treatment was as given in Example 15.

Results of Flameproofing Tests

According the German Industrial Standard Test 53906 for flammability, better results were obtained with the samples finished as described in Examples 14 and 15 than with those finished with the known compounds as in Examples X, Y and Z. The test results are listed in Table 2.

Table 2

Results of flammability tests (German Industrial Standard 53906) with 67/33 % polyester/cotton blend fabric finished with five different flameproofing agents

| Finish | Flammable | Burning time in sec. | Carbonized/ burnt surface (%) |
|---|---|---|---|
| Unfinished blend fabric | yes | 63.2 | 100 |
| Example 14 | | | |
| a) not washed | no | 0 | 3 |
| b) washed once | partly | 17.8 | 10 |
| c) washed 10 times | partly | 32.4 | 21 |
| Example 15 | | | |
| a) not washed | no | 0 | 6 |
| b) washed once | no | 0 | 6 |

Table 2-continued

| | | | |
|---|---|---|---|
| c) washed 10 times | partly | 87 | 50 |
| Example X | | | |
| a) not washed | yes | 99.4 | 56 |
| b) washed once | yes | 77.0 | 51 |
| c) washed 10 times | yes | 71.8 | 56 |
| Example Y | | | |
| a) not washed | yes | 85.8 | 27 |
| b) washed once | yes | 112.8 | 74 |
| c) washed 10 times | yes | 136.4 | 77 |
| Example Z | | | |
| a) not washed | partly | 50.0 | 23 |
| b) washed once | yes | 149.6 | 53 |
| c) washed 10 times | yes | 138.3 | 74 |

Having thus disclosed the invention what we claim is:

1. A compound of the formula $$\left[\begin{array}{c}Hal-CH_2\\ \\Hal-CH_2\end{array}\!\!\!\!\!\!C\!\!\!\!\!\!\begin{array}{c}CH_2-O\\ \\CH_2-O\end{array}\!\!\!\!\!\!\overset{(Y)_{m-1}}{\underset{\|}{P}}\!\!-\!Z\!\!-\!\!\right]_n\!\!R_1$$

in which
Hal signifies chlorine or bromine,
Y signifies oxygen or sulphur, and either
(a) m is 1, n is 1, Z is oxygen and $R_1$ is a radical

[structure: Hal-substituted phenyl or Hal—H$_2$C—C(CH$_2$Hal)$_2$—CH$_2$—]

in which Hal is as defined above, or
(b) m is 1, n is 2, Z is oxygen and $R_1$ is a radical

[structures: —CH$_2$—C(CH$_2$Hal)$_2$—CH$_2$—, tetrahal-phenylene, or bis(Hal-phenyl)isopropylidene]

in which Hal is as defined above, or
(c) m is 2, n is 1, Z is oxygen and $R_1$ is alkyl of 1 to 18 carbon atoms, alkyl of 1 to 6 carbon atoms substituted by up to 3 chlorine or bromine atoms, phenyl, diphenyl, α-naphthyl, β-naphthyl, phenyl substituted by up to 5 chlorine or bromine atoms, or cyclohexyl, or
(d) m is 2, n is 2, Z is oxygen and $R_1$ is a radical

[structures: cyclohexylene, phenylene]

[structures: tetrahal-phenylene, bis(Hal-phenyl)isopropylidene]

in which Hal is as defined above or

[structure: —C$_6$H$_4$—(L)$_{x-1}$—C$_6$H$_4$—]

in which L signifies —CH$_2$CH$_2$—, $$-\underset{CH_3}{\overset{CH_3}{\underset{|}{\overset{|}{C}}}}-,$$

oxygen, sulphur or —SO$_2$—, and x is 1 or 2.

2. A compound of claim 1, in which m is 1, n is 1, Z is oxygen, and $R_1$ is

[structure: Hal-substituted phenyl or Hal—H$_2$C—C(CH$_2$Hal)$_2$—CH$_2$—]

Hal is as defined in claim 1.

3. A compound of claim 2, in which Hal is bromine.

4. A compound of claim 1, in which m is 1, n is 2, Z is oxygen and $R_1$ is a radical

[structures: —CH$_2$—C(CH$_2$Hal)$_2$—CH$_2$—, tetrahal-phenylene, or bis(Hal-phenyl)isopropylidene]

5. A compound of claim 4, in which Hal is bromine.

6. A compound of claim 1, in which m is 2, n is 1, Z is oxygen and $R_1$ is alkyl of 1 to 18 carbon atoms, alkyl of 1 to 6 carbon atoms substituted by up to 3 chlorine or bromine atoms, phenyl, diphenyl, α-naphthyl, β-naphthyl or phenyl substituted by up to 5 chlorine or bromine atoms.

7. A compound of claim 6, in which $R_1$ is phenyl substituted by up to 5 chlorine or bromine atoms or alkyl of 1 to 6 carbon atoms substituted by up to 3 chlorine or bromine atoms.

8. A compound of claim 1, in which m is 2, n is 2, Z is oxygen and $R_1$ is a radical

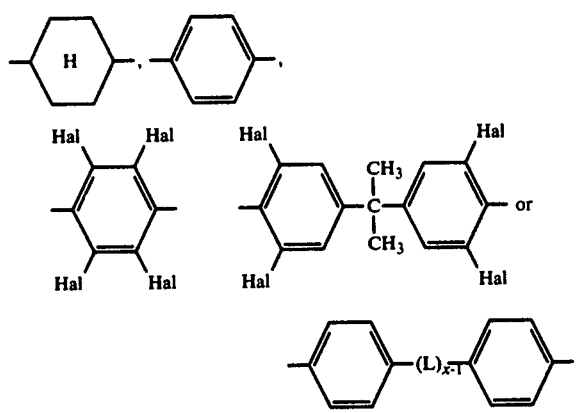

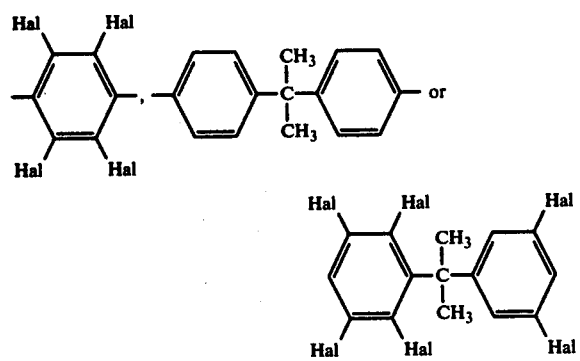

in which Hal, L and x are as defined in claim 1.

9. A compound of claim 8, in which $R_1$ is a radical

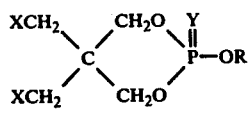

in which Hal is as defined in claim 8.

10. A compound of claim 9, in which Hal is bromine.
11. A compound of the formula

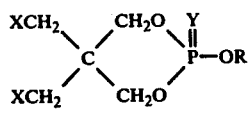

where
R is alkyl of 1 to 18 carbon atoms, haloalkyl of 1 to 6 carbon atoms, phenyl, halophenyl or cyclohexyl,
X is chlorine or bromine, and
Y is oxygen or sulfur.

12. A compound of the formula

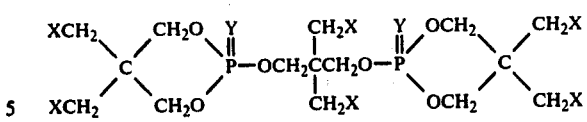

wherein X is chlorine or bromine, and Y is oxygen or sulfur.

13. The compound of claim 3 of the formula

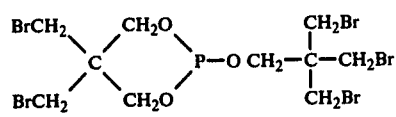

14. The compound of claim 4 of the formula

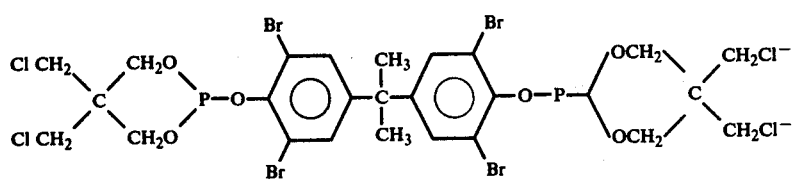

15. The compound of claim 4 of the formula

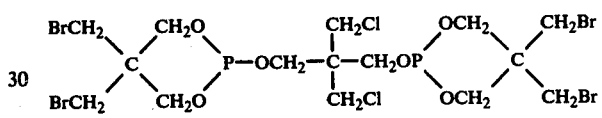

16. The compound of claim 4 of the formula

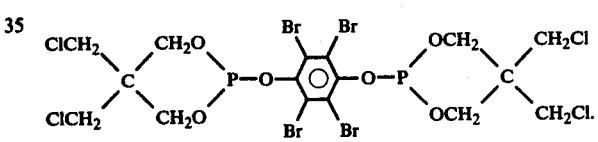

17. The compound according to claim 5 of the Formula

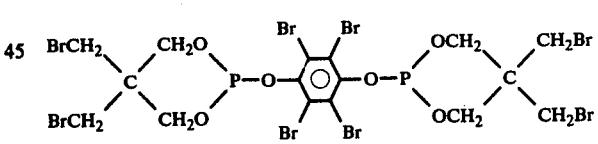

18. The compound according to claim 5 of the Formula

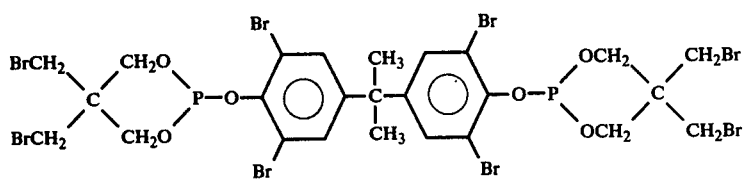

19. The compound according to claim 7 of the Formula

20. The compound according to claim 7 of the Formula
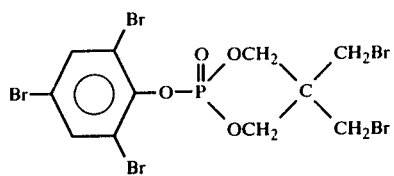
21. The compound according to claim 7 of the Formula
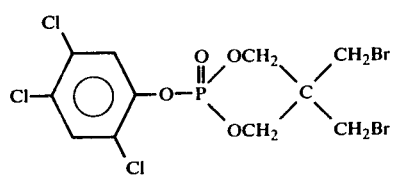
22. The compound of claim 7 of the formula
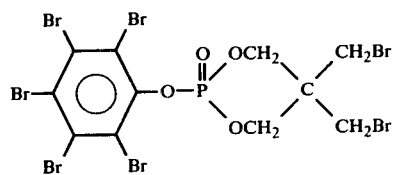
23. The compound of claim 7 of the formula
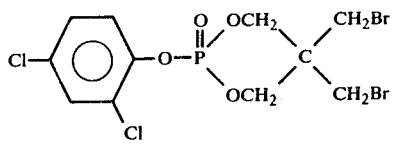
24. The compound of claim 7 of the formula
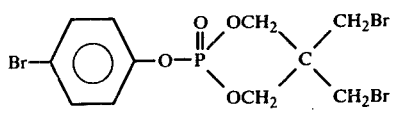
25. The compound of claim 10 of the formula
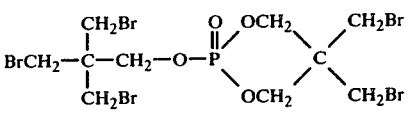
26. The compound of claim 10 of the formula
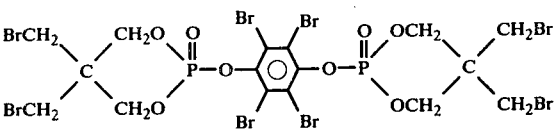
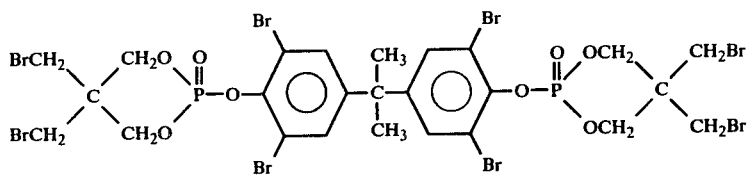
* * * * *